US006406716B2

(12) United States Patent
Caruso et al.

(10) Patent No.: US 6,406,716 B2
(45) Date of Patent: *Jun. 18, 2002

(54) ANTICONVULSANT CONTAINING COMPOSITION FOR TREATING NEUROPATHIC PAIN

(75) Inventors: Frank S. Caruso, Colts Neck, NJ (US); Fredrick L. Minn, Blue Bell, PA (US); John W. Lyle, Belmar, NJ (US)

(73) Assignee: Endo Pharmaceuticals Inc., Chadds Ford, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/780,858

(22) Filed: Feb. 9, 2001

Related U.S. Application Data

(63) Continuation of application No. 09/253,598, filed on Feb. 22, 1999, now Pat. No. 6,187,338, which is a continuation of application No. PCT/US97/14680, filed on Aug. 21, 1997.
(60) Provisional application No. 60/024,508, filed on Aug. 23, 1996.

(51) Int. Cl.[7] .............................. A61K 9/22; A61K 9/52
(52) U.S. Cl. ........................ 424/468; 424/455; 424/457; 424/464
(58) Field of Search ................................ 424/457, 468, 424/489, 455, 464, 423, 451, 456

(56) References Cited

U.S. PATENT DOCUMENTS

| 5,234,929 A | | 8/1993 | Chelen ........................ 514/269 |
| 6,057,373 A | * | 5/2000 | Fogel .......................... 514/740 |
| 6,187,338 B1 | * | 2/2001 | Caruso et al. ............... 424/468 |

FOREIGN PATENT DOCUMENTS

| EP | 0459695 A1 | 12/1991 |
| EP | 0615749 A2 | 8/1994 |
| WO | 8701036 | 2/1987 |
| WO | 8905641 | 6/1989 |
| WO | 8905642 | 6/1989 |

OTHER PUBLICATIONS

International Search Report for PCT/US 97/14680; International filing date Aug. 21, 1997.

\* cited by examiner

*Primary Examiner*—James M. Spear
(74) *Attorney, Agent, or Firm*—Dilworth & Barese, LLP

(57) ABSTRACT

The effectiveness of an anticonvulsant such as gabapentin for alleviating neuropathic pain is potentiated by a nontoxic antagonist for the N-methyl-D-aspartate receptor or nontoxic substance that blocks a major intracellular consequence of N-methyl-D-aspartate receptor activation.

46 Claims, No Drawings

ANTICONVULSANT CONTAINING COMPOSITION FOR TREATING NEUROPATHIC PAIN

This is a continuation of application Ser. No. 09/253,598 filed Feb. 22, 1999 now U.S. Pat. No. 6,187,338, which is a continuation of application Ser. No. PCT/US97/14680 filed Aug. 21, 1997. This application claims benefit under 35 U.S.C. §119(e) of U.S. Provisional Application No. 60/024,508 filed Aug. 23, 1996.

BACKGROUND OF THE INVENTION

This invention relates to a composition and method for alleviating neuropathic pain. More particularly, this invention is directed to a composition and method for alleviating neuropathic pain in which a neuropathic pain-alleviating amount of an anticonvulsant is combined with an anticonvulsant-potentiating amount of a nontoxic antagonist, or blocker, for the N-methyl-D-aspartate (NMDA) receptor or nontoxic substance that blocks a major intracellular consequence of NMDA receptor activation.

Neuropathic pain is pain that is due to functional abnormalities of the nervous system. Fields, "Pain", McGraw-Hill, Inc. (1987), pp. 133 et seq. There are a variety of possible mechanisms by which nerve dysfunction can cause neuropathic pain: hyperactivity in primary afferent or central nervous system (CNS) nociceptive neurons, loss of central inhibitory connections, and increased activity in sympathetic efferents. Neuropathic pain typically occurs following injury to elements of the nervous system involved in nociception, such as peripheral nerve injury, in which the lesions deafferent the nociceptive pathway, the resultant pain sometimes being referred to deafferentation pain. Neuropathic pain is much more likely to occur with peripheral than with central nervous system damage. Examples of causes of painful nerve injury are: accidental trauma, tumors, cerval or lumbar spine disease, and surgical procedures. These injuries usually involve one or two peripheral nerves or nerve roots, and the pain is felt in the body region normally innervated by the damaged nerves. Additionally, there are also toxic, metabolic, and hereditary causes of painful polyneuropathies, e.g., alcohol abuse, diabetes mellitus. These tend to be symmetrical and are most severe on the distal limbs.

SUMMARY OF THE INVENTION

In accordance with the present invention, a drug composition is provided which comprises a neuropathic pain-alleviating amount of at least one anticonvulsant in combination with an anticonvulsant-potentiating amount of at least one nontoxic antagonist for the NMDA receptor or nontoxic substance that blocks a major intracellular consequence of NMDA receptor activation.

Further in accordance with the present invention, a method of alleviating neuropathic pain is provided which comprises administering to a mammal exhibiting neuropathic pain (a) a neuropathic pain-alleviating amount of at least one anticonvulsant and (b) an anticonvulsant-potentiating amount of at least one nontoxic antagonist for the NMDA receptor or nontoxic substance that blocks a major intracellular consequence of NMDA receptor activation with (a) being administered prior to, with or following the administration of (b).

The expression "N-methyl-D-aspartate receptor" shall be understood to include all of the binding site subcategories associated with the NMDA receptor, e.g., the glycine-binding site, the phenylcyclidine (PCP)-binding site, etc., as well as the NMDA channel. Thus, the invention herein contemplates the use of nontoxic substances that block an NMDA receptor binding site, e.g., dextrorphan, or the NMDA channel, e.g., a source of magnesium such as magnesium sulfate.

The term "nontoxic" as used herein shall be understood in a relative sense and is intended to designate any substance that has been approved by the United States Food and Drug Administration ("FDA") for administration to humans or, in keeping with established regulatory criteria and practice, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 (the compound 5-methyl-10,11-dihydro-SH-dibenze[a,d]cyclohepten-5,10-imine), CPP (the compound 3-[2-carboxypiperazin-4-yl] propyl-1-phosphonic acid) and PCP (the compound 1-(1-phenylcyclohexyl)piperidine) whose toxicities effectively preclude their therapeutic use.

The expression "neuropathic pain-alleviating" shall be understood herein to include the expressions "neuropathic pain-suppressing" and "neuropathic pain-inhibiting" as the invention is applicable to the alleviation of existing neuropathic pain as well as the suppression or inhibition of neuropathic pain which would otherwise ensue from an imminent neuropathic pain-causing event.

DESCRIPTION OF THE PREFERRED EMBODIMENTS

Any of the pain-alleviating anticonvulsants can be used herein. For extensive listings of anticonvulsants, see, e.g., Goodman and Gilman's "The Pharmaceutical Basis Of Therapeutics", 8th ed., McGraw-Hill, Inc. (1990), pp. 436–462, and "Remington's Pharmaceutical Sciences", 17th ed., Mack Publishing Company (1985), pp. 1075–1083. Specific neuropathic pain-alleviating anticonvulsants that can be used herein include lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan.

Among the nontoxic substances that block the NMDA receptor and as such are useful for potentiating the neuropathic pain-alleviating activity of the anticonvulsant in accordance with this invention are dextromethorphan ((+)-3-hydroxy-N-methylmorphinan), its metabolite dextrorphan ((+)-3-hydroxy-N-methylmorphinan), amantadine (1-amino adamantine), memantine (3,5 dimethylaminoadamantone), their mixtures and their pharmaceutically acceptable salts. Other useful nontoxic substances that block the NMDA receptor include pyrroloquinoline quinone and cis-4-(phosphonomethyl)-2-piperidinecarboxylic acid.

In addition to, or in place of, a blocker for the NMDA receptor, at least one nontoxic substance that blocks a major intracellular consequence of NMDA receptor activation can also be used. Activation of the NMDA receptor, a subtype of excitatory amino acid receptors, induces a number of changes in the functional activity of nerve cells and, in particular, their capacity for excitability or inhibition in the presence of an addictive substance via an increase in intracellular Ca++ concentration. The major consequences of NMDA receptor activation include the following sequences, or cascades, of events occurring within nerve cells:

a) translocation and activation of protein kinases such as protein kinase C→phosphorylation of substrate proteins such as cytosolic enzymes, channel proteins, receptor proteins, etc.→changes in functional activity;

b) initiation of early gene (c-fos, c-jun, zif-268, etc.) expression by either increased intracellular Ca++ or Ca++-activated protein kinases→expression of functional genes responsible for production of cellular enzymes (such as protein kinases), receptor proteins (such as the NMDA receptor), ion channel proteins (such as K+, Na+, Ca++ channels), neuropeptides (such as dynorphin), etc.→changes in functional activity;

c) Ca++/calmodulin (or other Ca++ binding proteins) induced activation of enzymes and other cellular components→activation of Ca++/calmodulin-protein kinase systems such as Ca++/calmodulin kinase II→autophosphorylation of enzymes (e.g., Ca++/calmodulin kinase II) or other functional proteins→changes in functional activity;

d) Ca++/calmodulin induced activation of constitutive nitric oxide synthase as well as induction of inducible nitric oxide synthase→production of nitric oxide→i) production of cyclic guanosine monophosphate via activation of guanosine cyclase resulting in activation of protein kinases and early gene expression; ii) direct protein modification such as enzymes, receptor and/or channel proteins; iii) lipid membrane modification and/or nucleic acid modification via scavenge of free radicals; iv) induction of neurotoxicity at higher nitric oxide levels; v) retrograde actions in adjacent neurons or glial cells such as facilitation of glutamate release/NMDA receptor activation and/or inhibition of post-synaptic NMDA receptors→changes in functional activity;

e) interactions with the cyclic adenosine monophosphate/protein kinase A system, the phospholipase C-inositol triphosphate-Ca++/diacylglycerol-protein kinase system, the phospholipase A2-arachidonic acid/prostanoids/leukotrienes system→changes in functional activity induced by second messenger systems other than NMDA receptor/Ca++/Ca++-calmodulin/protein kinase systems; and, f) interactions with other excitatory amino acid receptor subtypes including non-NMDA receptors and metabotropic receptors as well as intracellular events subsequent to the activation of these excitatory amino acid receptor subtypes→changes in functional activity induced by the non-NMDA and metabotropic receptor activation.

A substance that blocks the NMDA receptor will effectively prevent all of the foregoing major intracellular sequences of events from taking place. However, even with activation of the NMDA receptor, it is still possible to treat neuropathic pain in accordance with this invention by administering the anticonvulsant and a nontoxic substance that blocks at least one of the foregoing major intracellular sequences of events brought about by activation of the NMDA receptor. Thus, e.g., a substance that interferes with translocation and activation of protein kinase C or with calmodulin induced activation of constitutive nitric oxide synthase as well as induction of inducible nitric oxide synthase is also useful for the practice of this invention.

Nontoxic substances that block a major intracellular consequence of NMDA receptor activation and are therefore useful in the practice of the invention include inhibitors of protein kinase C, e.g., gangliosides such as ganglioside $GM_1$ (monosialoganglioside) and ganglioside $GT_{1b}$ (trisialoganglioside); amphipathic long chain bases such as sphingosine, N,N,N-trimethylsphingosine, sphinganine and psychosine; quinolyloxazole-2-ones such as 4-methyl-5-(3-quinolinyl)-2-(3H)-oxazolone and phenyl-5-(2-quinolinyl)-2-3(3H)-oxazolone; 1,4-bis-(amino-hydroxyalkylamino)-anthraquinones such as 1,4-bis-(3-propylamino-2-hydroxypropylamino)-9,10anthracenedione and 1,4-bis-(3-benzylamino-2-hydroxypropylamino)-9,10anthracenedione; and, mixtures and pharmaceutically acceptable salts of any of the foregoing.

Additional nontoxic substances that block a major intracellular consequence of NMDA receptor activation and as such are useful in the practice of the invention include inhibitors of calmodulin, such as the phenothiazines, in particular, chlorpromazine, chlorpromazine sulfoxide, prochlorperazine dimaleate, perphenazine, trifluoperazine, fluphenazine, fluphenazine enanthate, fluphenazine decanoate, thioridazine, mesoridazine besylate, piperacetazine, acetophenazine dimaleate, carphenazine dimaleate, butaperazine dimaleate and phenothiazine sulfoxide; naphthalenesulfonamides such as N-(6-aminohexyl)-5-chloro-1-naphthalenesulfonamide, N-(6-aminohexyl)-5-chloro-2-naphthalenesulfonamide and N-(6-aminohexyl)-5-bromo-2-naphthalenesulfonamide; 4-substituted-4H,6H-pyrrolo[1,2-a][4,1]benzoxazepines such as 1,3-dihydro-1-{1-[(4-methyl-4H,6H-pyrrolo[1,2-a][4,1]benzoxazepin-4-yl)methyl]-4-piperidinyl}-2H-benzimidazol-2-one; benzhydryls such as N-[2](diphenylmethylthioethyl]-2-(trifluoromethyl)benzeneethanamine, N-[2-(bis(4-fluorophenyl) methylthio)ethyl]-2-(trifluoromethyl)benzeneethanamine and N-[2-(bis(4-fluorophenyl)methylthio)ethyl]-3-(trifluoromethyl)benzeneethanamine; tricyclic antidepressant drugs such as imipramine, 2-chloroimipramine and amitriptyline; penfluridol; haloperidol; pimozide; clozapine; calmidazolin; and, mixtures and pharmaceutically acceptable salts of any of the foregoing.

Of the two groups, the NMDA-receptor antagonists are preferred and of these, dextromethorphan is especially preferred due to its wide use in over-the-counter medications where it functions as a cough suppressant.

With regard to dosage levels, the anticonvulsant must be present in a neuropathic pain-alleviating amount, e.g., at a level corresponding to the generally recommended adult human dosages for a particular anticonvulsant, and the NMDA receptor blocker or substance that blocks a major intracellular consequence of NMDA activation must be present at a level that potentiates the neuropathic pain-alleviating effectiveness of the anticonvulsant. Specific dosage levels for the anticonvulsants that can be used herein as given, inter alia, in the "Physicians' Desk Reference", 1996 Edition (Medical Economics Data Production Company, Montvale, N.J.) as well as in other reference works including Goodman and Gilman's "The Pharmaceutical Basis of Therapeutics" and "Remington's Pharmaceutical Sciences" both of which as referred to above. Given the wide variation in dosage level of the anticonvulsant which depends to a large extent on the specific anticonvulsant being administered, there can similarly be a wide variation in the dosage level of the NMDA receptor blocker or substance that blocks a major intracellular consequence of NMDA receptor activation. These amounts can be determined for a particular drug combination in accordance with this invention employing routine experimental testing. In case of the anticonvulsant phenobarbital and the NMDA receptor blocker dextromethorphan, dosages of from 50 to 300 mg/day of the former coadministered with from 30 to 120 mg/day of the latter will usually provide acceptable results.

While the neuropathic pain-alleviating anticonvulsant and anticonvulsant-potentiating nontoxic NMDA receptor blocker or nontoxic substance that blocks a major intracellular consequence of NMDA receptor activation need not be administered together, they must both be present in the patient at effective levels at the same time. While it is within the scope of the invention to separately administer the anticonvulsant and the NMDA receptor blocker or nontoxic substance that blocks a major intracellular consequence of NMDA receptor activation, as a matter of convenience, it is preferred that these drugs be coadministered in a single dosage form. All modes of administrations are contemplated, e.g., orally, rectally, parenterally, intranasally and topically.

A therapeutic composition containing the anticonvulsant and nontoxic NMDA receptor blocker or nontoxic substance that blocks a major intracellular consequence of NMDA receptor activation will ordinarily be formulated with one or more pharmaceutically acceptable ingredients in accordance with known and established practice. Thus, the composition can be formulated as a liquid, powder, elixir, injectable solution, etc. Formulations for oral use can be provided as tablets or hard capsules wherein the pharmacologically active ingredients are mixed with an inert solid diluent such as calcium carbonate, calcium phosphate or kaolin, or as soft gelatin capsules wherein the active ingredients are mixed with an oleaginous medium, e.g., liquid paraffin or olive oil.

Aqueous suspensions can include pharmaceutically acceptable excipients such as suspending agents,.e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation, products of an alkylene oxide with fatty acids, e.g., polyoxyethylene stearate, or condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

In addition to anticonvulsant and nontoxic NMDA receptor blocker or nontoxic substance that blocks a manor intracellular consequence of NMDA receptor activation, the therapeutic composition herein can optionally contain at least one other pharmacologically active substance e.g., a non-narcotic analgesic such as acetaminophen or a non-steroidal anti-inflammatory drug (NSAID) such as aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and the like.

What is claimed is:

1. A neuropathic pain-alleviating composition for administration to a mammal exhibiting, or about to exhibit, neuropathic pain which comprises (a) gabapentin and (b) at least one nontoxic antagonist for the N-methyl-D-aspartate receptor or nontoxic substance that blocks a major intracellular consequence of N-methyl-D-aspartate receptor activation, the combined amount of (a) and (b) in the composition being a neuropathic pain-alleviating amount and the amount of (b) in the composition being sufficient to potentiate the neuropathic pain-alleviating effectiveness of (a).

2. The composition of claim 1 wherein (b) is at least one member selected from the group consisting of dextromethorphan, dextrorphan, amantadine, memantine and pharmaceutically acceptable salt thereof.

3. The composition of claim 1 wherein (a) and (b) each is present in a sustained release carrier.

4. A neuropathic pain-alleviating composition for administration to a mammal exhibiting, or about to exhibit, neuropathic pain which comprises (a) at least one member selected from the group consisting of lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan, (b) at least one nontoxic antagonist for the N-methyl-D-aspartate receptor or nontoxic substance that blocks a major intracellular consequence of N-methyl-D-aspartate receptor activation and (c) at least one analgesic, the combined amount of (a) and (b) in the composition being a neuropathic pain-alleviating amount and the amount of (b) in the composition being sufficient to potentiate the neuropathic pain-alleviating effectiveness of (a).

5. The composition of claim 4 wherein (b) is at least one member selected from the group consisting of dextromethorphan, dextrorphan, amantadine, memantine and pharmaceutically acceptable salt thereof.

6. The composition of claim 5 wherein analgesic (c) is a non-narcotic analgesic.

7. The composition of claim 6 wherein non-narcotic analgesic (c) is at least one member selected from the group consisting of acetaminophen and nonsteroidal anti-inflammatory drug.

8. The composition of claim 7 wherein the nonsteroidal anti-inflammatory drug is at least one member selected from the group consisting of aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxican, sulindac, tolmetin and zomepirac.

9. A method of alleviating neuropathic pain in a mammal exhibiting, or about to exhibit, neuropathic pain which comprises administering to the mammal a neuropathic pain-alleviating composition which comprises (a) gabapentin and (b) at least one nontoxic antagonist for the N-methyl-D-aspartate receptor or nontoxic substance that blocks a major intracellular consequence of N-methyl-D-aspartate receptor activation, the combined amount of (a) and (b) in the composition being a neuropathic pain-alleviating amount and the amount of (b) in the composition being sufficient to potentiate the neuropathic pain-alleviating effectiveness of (a).

10. The method of claim 9 wherein (b) is at least one member selected from the group consisting of dextromethorphan, dextrorphan, amantadine, memantine and pharmaceutically acceptable salt thereof.

11. The method of claim 9 wherein (a) and (b) each is present in a sustained release carrier.

12. A method of alleviating neuropathic pain in a mammal exhibiting, or about to exhibit, neuropathic pain which comprises administering to the mammal a neuropathic pain-alleviating composition which comprises (a) at least one member selected from the group consisting of lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan, (b) at least one nontoxic antagonist for the N-methyl-D-aspartate receptor or nontoxic substance that blocks a major intracellular consequence of N-methyl-D-aspartate receptor activation and (c) at least one analgesic, the combined amount of (a) and (b) in the composition being a neuropathic pain-alleviating amount and the amount of (b) in the composition being sufficient to potentiate the neuropathic pain-alleviating effectiveness of (a).

13. The method of claim 12 wherein (b) is at least one member selected from the group consisting of dextromethorphan, dextrorphan, amantadine, memantine and pharmaceutically acceptable salt thereof.

14. The method of claim 12 wherein analgesic (c) is a non-narcotic analgesic.

15. The method of claim 14 wherein non-narcotic analgesic (c) is at least one member selected from the group consisting of acetaminophen and nonsteroidal anti-inflammatory drug.

16. The method of claim 15 wherein the nonsteroidal anti-inflammatory drug is at least one member selected from the group consisting of aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxican, sulindac, tolmetin and zomepirac.

17. A method of alleviating neuropathic pain in a mammal exhibiting, or about to exhibit, neuropathic pain caused by accidental trauma which comprises administering to the mammal a neuropathic pain-alleviating composition which comprises (a) gabapentin and (b) at least one nontoxic antagonist for the N-methyl-D-aspartate receptor or nontoxic substance that blocks a major intracellular consequence of N-methyl-D-aspartate receptor activation, the combined amount of (a) and (b) in the composition being a neuropathic pain-alleviating amount and the amount of (b) in the composition being sufficient to potentiate the neuropathic pain-alleviating effectiveness of (a).

18. The method of claim 17 wherein (b) is at least one member selected from the group consisting of dextromethorphan, dextrorphan, amantadine, memantine and pharmaceutically acceptable salt thereof.

19. A method of alleviating neuropathic pain in a mammal exhibiting, or about to exhibit, neuropathic pain caused by accidental trauma which comprises administering to the mammal a neuropathic pain-alleviating composition which comprises (a) at least one member selected from the group consisting of lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan, (b) at least one nontoxic antagonist for the N-methyl-D-aspartate receptor or nontoxic substance that blocks a major intracellular consequence of N-methyl-D-aspartate receptor activation and (c) at least one analgesic, the combined amount of (a) and (b) in the composition being a neuropathic pain-alleviating amount and the amount of (b) in the composition being sufficient to potentiate the neuropathic pain-alleviating effectiveness of (a).

20. The method of claim 19 wherein (b) is at least one member selected from the group consisting of dextromethorphan, dextrorphan, amantadine, memantine and pharmaceutically acceptable salt thereof.

21. The method of claim 20 wherein analgesic (c) is a non-narcotic analgesic.

22. The method of claim 21 wherein non-narcotic analgesic (c) is at least one member selected from the group consisting of acetaminophen and nonsteroidal anti-inflammatory drug.

23. A method of alleviating neuropathic pain in a mammal exhibiting, or about to exhibit, neuropathic pain caused by a tumor which comprises administering to the mammal a neuropathic pain-alleviating composition which comprises (a) gabapentin and (b) at least one nontoxic antagonist for the N-methyl-D-aspartate receptor or nontoxic substance that blocks a major intracellular consequence of N-methyl-D-aspartate receptor activation, the combined amount of (a) and (b) in the composition being a neuropathic pain-alleviating amount and the amount of (b) in the composition being sufficient to potentiate the neuropathic pain-alleviating effectiveness of (a).

24. The method of claim 23 wherein (b) is at least one member selected from the group consisting of dextromethorphan, dextrorphan, amantadine, memantine and pharmaceutically acceptable salt thereof.

25. A method of alleviating neuropathic pain in a mammal exhibiting, or about to exhibit, neuropathic pain caused by a tumor which comprises administering to the mammal a neuropathic pain-alleviating composition which comprises (a) at least one member selected from the group consisting of lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan, (b) at least one nontoxic antagonist for the N-methyl-D-aspartate receptor or nontoxic substance that blocks a major intracellular consequence of N-methyl-D-aspartate receptor activation and (c) at least one analgesic, the combined amount of (a) and (b) in the composition being a neuropathic pain-alleviating amount and the amount of (b) in the composition being sufficient to potentiate the neuropathic pain-alleviating effectiveness of (a).

26. The method of claim 23 wherein (b) is at least one member selected from the group consisting of dextromethorphan, dextrorphan, amantadine, memantine and pharmaceutically acceptable salt thereof.

27. The method of claim 26 wherein analgesic (c) is a non-narcotic analgesic.

28. The method of claim 27 wherein non-narcotic analgesic (c) is at least one member selected from the group consisting of acetaminophen and nonsteroidal anti-inflammatory drug.

29. A method of alleviating neuropathic pain in a mammal exhibiting, or about to exhibit, neuropathic pain caused by cervical spine disease which comprises administering to the mammal a neuropathic pain-alleviating composition which comprises (a) gabapentin and (b) at least one nontoxic antagonist for the N-methyl-D-aspartate receptor or nontoxic substance that blocks a major intracellular consequence of N-methyl-D-aspartate receptor activation, the combined amount of (a) and (b) in the composition being a neuropathic pain-alleviating amount and the amount of (b) in the composition being sufficient to potentiate the neuropathic pain-alleviating effectiveness of (a).

30. The method of claim 29 wherein (b) is at least one member selected from the group consisting of dextromethorphan, dextrorphan, amantadine, memantine and pharmaceutically acceptable salt thereof.

31. A method of alleviating neuropathic pain in a mammal exhibiting, or about to exhibit, neuropathic pain caused by cervical spine disease which comprises administering to the mammal a neuropathic pain-alleviating composition which comprises (a) at least one member selected from the group consisting of lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan, (b) at least one nontoxic antagonist for the N-methyl-D-aspartate receptor or nontoxic substance that blocks a major intracellular consequence of N-methyl-D-aspartate receptor activation and (c) at least one analgesic, the combined amount of (a) and (b) in the composition being a neuropathic pain-alleviating amount and the amount of (b) in the composition being sufficient to potentiate the neuropathic pain-alleviating effectiveness of (a).

32. The method of claim 31 wherein (b) is at least one member selected from the group consisting of dextromethorphan, dextrorphan, amantadine, memantine and pharmaceutically acceptable salt thereof.

33. The method of claim 32 wherein analgesic (c) is a non-narcotic analgesic.

34. The method of claim 33 wherein non-narcotic analgesic (c) is at least one member selected from the group consisting of acetaminophen and nonsteroidal anti-inflammatory drug.

35. A method of alleviating neuropathic pain in a mammal exhibiting, or about to exhibit, neuropathic pain caused by lumbar spine disease which comprises administering to the mammal a neuropathic pain-alleviating composition which comprises (a) gabapentin and (b) at least one nontoxic antagonist for the N-methyl-D-aspartate receptor or nontoxic substance that blocks a major intracellular consequence of N-methyl-D-aspartate receptor activation, the combined amount of (a) and (b) in the composition being a neuropathic pain-alleviating amount and the amount of (b) in the composition being sufficient to potentiate the neuropathic pain-alleviating effectiveness of (a).

36. The method of claim 35 wherein (b) is at least one member selected from the group consisting of dextromethorphan, dextrorphan, amantadine, memantine and pharmaceutically acceptable salt thereof.

37. A method of alleviating neuropathic pain in a mammal exhibiting, or about to exhibit, neuropathic pain caused by lumbar spine disease which comprises administering to the mammal a neuropathic pain-alleviating composition which comprises (a) at least one member selected from the group consisting of lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan, (b) at least one nontoxic antagonist for the N-methyl-D-aspartate receptor or nontoxic substance that blocks a major intracellular consequence of N-methyl-D-aspartate receptor activation and (c) at least one analgesic, the combined amount of (a) and (b) in the composition being a neuropathic pain-alleviating amount and the amount of (b) in the composition being sufficient to potentiate the neuropathic pain-alleviating effectiveness of (a).

38. The method of claim 37 wherein (b) is at least one member selected from the group consisting of dextromethorphan, dextrorphan, amantadine, memantine and pharmaceutically acceptable salt thereof.

39. The method of claim 38 wherein analgesic (c) is a non-narcotic analgesic.

40. The method of claim 39 wherein non-narcotic analgesic (c) is at least one member selected from the group consisting of acetaminophen and nonsteroidal anti-inflammatory drug.

41. A method of alleviating neuropathic pain in a mammal exhibiting, or about to exhibit, neuropathic pain caused by painful neuropathy which comprises administering to the mammal a neuropathic pain-alleviating composition which comprises (a) gabapentin and (b) at least one nontoxic antagonist for the N-methyl-D-aspartate receptor or nontoxic substance that blocks a major intracellular consequence of N-methyl-D-aspartate receptor activation, the combined amount of (a) and (b) in the composition being a neuropathic pain-alleviating amount and the amount of (b) in the composition being sufficient to potentiate the neuropathic pain-alleviating effectiveness of (a).

42. The method of claim 41 wherein (b) is at least one member selected from the group consisting of dextromethorphan, dextrorphan, amantadine, memantine and pharmaceutically acceptable salt thereof.

43. A method of alleviating neuropathic pain in a mammal exhibiting, or about to exhibit, neuropathic pain caused by a painful neuropathy which comprises administering to the mammal a neuropathic pain-alleviating composition which comprises (a) at least one member selected from the group consisting of lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan, (b) at least one nontoxic antagonist for the N-methyl-D-aspartate receptor or nontoxic substance that blocks a major intracellular consequence of N-methyl- D-aspartate receptor activation and (c) at least one analgesic, the combined amount of (a) and (b) in the composition being a neuropathic pain-alleviating amount and the amount of (b) in the composition being sufficient to potentiate the neuropathic pain-alleviating effectiveness of (a).

44. The method of claim 43 wherein (b) is at least one member selected from the group consisting of dextromethorphan, dextrorphan, amantadine, memantine and pharmaceutically acceptable salt thereof.

45. The method of claim 44 wherein analgesic (c) is a non-narcotic analgesic.

46. The method of claim 45 wherein non-narcotic analgesic (c) is at least one member selected from the group consisting of acetaminophen and nonsteroidal anti-inflammatory drug.

* * * * *

UNITED STATES PATENT AND TRADEMARK OFFICE
CERTIFICATE OF CORRECTION

PATENT NO. : 6,406,716 B2  Page 1 of 1
DATED : June 18, 2002
INVENTOR(S) : Caruso et al.

It is certified that error appears in the above-identified patent and that said Letters Patent is hereby corrected as shown below:

Title page,
Item [56], FOREIGN PATENT DOCUMENTS, "EP 0615749 A2 8/1994" should be
-- EP 0615749 A2 9/1994 --
Item [74], *Attorney, Agent, or Firm*: "Dilworth & Barese, LLP" should be -- Dilworth & Barrese, LLP --

Column 1,
Line 25, "et seq." should be -- et seq. --

Column 2,
Line 17, "5-methyl-10,11-dihydro-SH-dibenze[a,d]cyclohepten-5,10-" should be
-- 5-methyl-10,11-dihydro-SH-dibenze[a,d] cyclohepten-5,10 --

Column 3,
Line 9, "(c-fos, c-jun, zif-268, etc.)" should be -- (*c-fos, c-jun, zif*-268, etc.

Column 4,
Line 12, "hydroxypropylamino)-9,10anthracenedione" should be
-- hydroxypropylamino)-9,10 anthracenedione --
Line 14, "10anthracenedione;" should be -- 10 anthracenedione; --
Line 34, "(dipehnylmethylthioethyl]-2-(trifluoromethyl)" should be
-- (diphenylmethylthioethyl]-2-(trifluoromethyl) --
Line 35, "N-[2-(bis(4-fluorophenyl) methylthio)" should be
-- N-[2-(bis(4-fluorophenyl)methylthio) --
Line 56, "inter alia" should be -- inter alia --

Signed and Sealed this

Twenty-eighth Day of January, 2003

JAMES E. ROGAN
*Director of the United States Patent and Trademark Office*